(12) United States Patent
Noras

(10) Patent No.: US 9,943,435 B2
(45) Date of Patent: Apr. 17, 2018

(54) HEAD RESTRAINER FOR IMMOBILIZING THE HEAD OF PATIENTS

(71) Applicant: Hubert Noras, Würzburg (DE)

(72) Inventor: Hubert Noras, Würzburg (DE)

( * ) Notice: Subject to any disclaimer, the term of this patent is extended or adjusted under 35 U.S.C. 154(b) by 120 days.

(21) Appl. No.: 14/401,119

(22) PCT Filed: May 8, 2013

(86) PCT No.: PCT/DE2013/100172
§ 371 (c)(1),
(2) Date: Nov. 14, 2014

(87) PCT Pub. No.: WO2013/170852
PCT Pub. Date: Nov. 21, 2013

(65) Prior Publication Data
US 2015/0096570 A1  Apr. 9, 2015

(30) Foreign Application Priority Data

May 15, 2012 (DE) .......................... 10 2012 009 584

(51) Int. Cl.
| | | |
|---|---|---|
| *A61G 13/12* | (2006.01) | |
| *A61F 5/37* | (2006.01) | |
| *A61B 5/055* | (2006.01) | |
| *A61B 5/00* | (2006.01) | |
| *A61B 90/14* | (2016.01) | |

(52) U.S. Cl.
CPC .......... *A61F 5/3707* (2013.01); *A61B 5/0555* (2013.01); *A61B 5/6814* (2013.01); *A61B 90/14* (2016.02)

(58) Field of Classification Search
CPC ....... A61B 5/0555; A61B 5/6814; A61B 5/04; A61B 90/14; A61B 90/11; A61B 19/203;
(Continued)

(56) References Cited

U.S. PATENT DOCUMENTS 5,269,034 A * 12/1993 Day ...................... A61B 90/14
  403/59
5,290,220 A * 3/1994 Guhl ........................ A61F 5/04
  128/882
(Continued)

FOREIGN PATENT DOCUMENTS

DE  9210457 U1  10/1992
DE  19718535 A1  11/1998
(Continued)

OTHER PUBLICATIONS

International Search Report (ISR) with regard to PCT/DE2013/100172 as completed by the EPO on Sep. 6, 2013 and dated Sep. 17, 2013.

*Primary Examiner* — Ophelia A Hawthorne
(74) *Attorney, Agent, or Firm* — Westman, Champlin & Koehler, P.A.

(57) ABSTRACT

Head restrainer for immobilizing the head of patients for producing NMR images such as those which are based on the application of electromagnetic beams (X-rays, gamma rays) and/or for carrying out surgical procedures, having a C-bend (1), at each end region of which at least one mandrel (3) is attached, these being substantially diametrically assigned with respect to each other, wherein at least one mandrel (3) is coaxially attached to an axially moveable bolt (2) which can be acted upon in the axial direction via a clamping device (11), and a force indicator (12) assigned to the clamping device, wherein fixing means (14) are provided which serve to temporarily set the bolt (2) and the attachment of the clamping device (11) and force indicator (12) to the head restrainer is releasable while the fixing arrangement is retained.

20 Claims, 2 Drawing Sheets

(58) Field of Classification Search
CPC . A61B 90/10; A61B 2090/101; A61F 5/3707;
A61F 5/37; A61F 5/3737; A61G 13/121;
A61G 13/128; A61G 13/1265; A61G
13/127; A61G 13/129; A61G 7/1084;
A61G 7/072; A61G 13/12
USPC ........ 606/130, 1, 6, 107, 54; 602/32, 34, 17,
602/33, 36, 40; 5/622, 636, 637, 640,
5/643; 600/417, 429
See application file for complete search history.

(56) References Cited

U.S. PATENT DOCUMENTS

| | | | |
|---|---|---|---|
| 5,347,894 A | | 9/1994 | Fischer |
| 5,537,704 A | * | 7/1996 | Dinkler .................. A61B 90/14 |
| | | | 5/622 |
| 6,306,146 B1 | * | 10/2001 | Dinkler .................. A61B 90/11 |
| | | | 600/417 |
| 6,942,664 B1 | * | 9/2005 | Voor .................... A61B 17/645 |
| | | | 606/54 |
| 7,730,563 B1 | * | 6/2010 | Sklar ...................... A61B 90/14 |
| | | | 5/622 |
| 2005/0075650 A1 | * | 4/2005 | Dinkler .................. A61B 90/14 |
| | | | 606/130 |
| 2012/0060847 A1 | * | 3/2012 | Stratton ............... A61B 19/203 |
| | | | 128/845 |

FOREIGN PATENT DOCUMENTS

| | | |
|---|---|---|
| DE | 202004006726 U1 | 6/2004 |
| DE | 102007052866 A1 | 8/2008 |
| DE | 102008022968 A1 | 8/2009 |

* cited by examiner

HEAD RESTRAINER FOR IMMOBILIZING THE HEAD OF PATIENTS

The invention relates to a head holder for fixation of the head of patients for producing nuclear magnetic resonance (NMR) images as well as images based on the application of electromagnetic beams (X-rays, gamma rays) and/or for carrying out surgical procedures, having a C-bend, at each end region of which at least one mandrel is fastened, these being substantially diametrically assigned with respect to each other, wherein at least one mandrel is coaxially fastened to an axially moveable bolt which can be acted upon in the axial direction via a clamping device, and a force indicator assigned to the clamping device.

The invention relates to a head holder for fixation of the head of patients for producing NMR images and/or X-ray images or else for carrying out surgical, in particular neurosurgical procedures. In such cases it is particularly to be ensured that, after fixation of the head, the regular change of orientation of the patient table by pivoting leads to displacements of the patient under the influence of gravity and nevertheless the fixation of the head must be retained. Furthermore, it is to be ensured that the fixation of the head can take place with a defined contact pressure. The head holders, which can be used for purposes that are already familiar, therefore consists, in their basic construction, of a C-bend, on the end of which at least one mandrel is attached in such a manner that the two mandrels are disposed in a diametrical alignment, one of the mandrels being axially movable for fixation of the head by adapting to different anatomical dimensions. To generate a defined contact pressure, at least one of the mandrels is guided on an axially movable bolt which in turn is acted on axially via a spring application, displays for reproduction of the instantaneous contact pressure being present. By this means a check and defined adjustment of the contact pressure becomes possible. In the solutions of this generic kind, this is often carried out in that a pin, which faces outward in an axial direction and which passes through the counter-holder of the spring as far as the outside, is fastened on the bolt, said spring being adjustable in its position, which is defined relative to the axis of the bolt, via a hollow-cylindrical screw-thread sleeve, so that in this manner the contact pressure of the spring is varied. At a high compression of the spring, the distance between the bolt and counter-holder becomes smaller, with the consequence that the pin projects outwardly by a greater amount. In the reverse case, the pin will only project by a correspondingly smaller distance. The projecting length of the pin is thus a direct measure of the contact pressure of the bolt, and thereby of the mandrel on the head of the patient. For fixation, the contact pressure is varied by rotating the sleeve to the extent that it assumes the defined value.

The devices of this generic kind are subject to disadvantages in several ways. Because of the necessary for relative movement between the individual mechanical parts, which include the axial displaceability of the bolt, the screw connections for adjusting the spring pressure and the relative movement of the sleeve with the counter-holder located therein, the necessity exists, even with high production accuracy, for play between the parts that are to be moved relative to one another. This leads, in the event of a change of the forces acting on the mandrel, to displacements of the patient, in the event of adjustment of the table, being unavoidable, even after fixation has been carried out. An intensification of these influences takes place in that, because of the necessary of play for movement of the pin, as well as of the spring, the pressure indicator would additionally lead to inaccuracies. Furthermore, it is to be regarded as a disadvantage that the exterior dimensions of this apparatus, which is present even during the surgical intervention, occupy a high intrinsic space, which disadvantageously makes accessibility for the operator more difficult. One of the causes of the bulky arrangement is the necessity for a corresponding spring travel, which is necessary to transfer the mandrel into the necessary positions, that is to say from the unloaded into the loaded state.

The purpose underlying the invention thus consists in developing head holders of this kind such that, while maintaining the possibility of fixation of the head with the aid of a defined contact pressure, to eliminate inaccuracies and permit a more compact construction of the head holder.

This object is achieved according to the invention in that fixation means are provided, which serve for temporary arresting of the bolt and that, while maintaining the fixation, the fastening of the clamping device and force display on the head holder is detachable.

This solution is effected in the gist of the invention by the provision of two features. On one hand, fixation means are provided, of which the concrete mechanical implementation is basically free within the scope of the invention, in so far as their purpose, namely the temporary possibility of fixation of the bolt can be realized. Another crucial teaching of the invention provides for the possibility of detaching the clamping device and force indicator from the head holder itself, wherein naturally the term "head holder" in this context is no longer intended to comprise the clamping device and force indicator. Here, too, in the most general case of the inventive idea, the specific embodiment of the detachable fastening of the clamping device and/or force indicator is arbitrary.

The set-up according to the invention permits the following procedure: the first steps consist, in a manner known per se, of the fact that the head of the patient is positioned in the head holder, subsequently at least one mandrel is moved onto the head of the patient, specifically to the extent that the desired contact pressure is reached. The monitoring of the clamping pressure as far as the maximum pressure is performed by means of the force indicator. Besides this procedure, which is known in the prior art and therefore does not require further explanation, the following two steps follow crucially. When the desired contact pressing force is reached, the bolt, and consequently the mandrel fastened therein, are arrested by the activation of a fixation means. The result is that the position of the bolt remains spatially fixed during the chronologically following work steps. At the outset, it was mentioned that, during the tilting, which is generally necessary, the patients experience, under the influence of gravity, a change of the contact pressure, which disadvantageously lead not only to a change of the contact pressure per se, but also, in the case of certain clamping devices, which include the widespread contact pressures generated with the aid of spring force, to a change of the position of the bolt or of the mandrel. The play that is present in the device contributes to this in the same manner. The fixing now has the decisive advantage that the spatial position of the bolt remains secured during the subsequent work phase, and the previous influences, which gave occasion for inaccuracies in imaging processes and/or deviations in the positioning during operative interventions, can be reliably eliminated. Due to the fixation of the bolt, the necessity of applying force via the clamping device ends, since the desired contact pressure has been achieved and the force indicator is no longer required in its function. This technical situation permits a further decisive step to be taken, namely to separate the clamping device and force indicator from the (remaining) head holder.

In order to allow the above-described work steps to be performed for the next patient, the clamping device and force indicator can be fastened on the head holder again, so that the removal thereof must therefore be temporary and thereby detachable. Subsequently the images are prepared and/or the surgical interventions are made.

The advantages that are achieved by implementing the teaching according to the invention are manifold:

The arresting of the bolt, which takes place through application of the fixation means, leads to the complete freedom from play thereof, so that, on adjustment of the table or of the trepanation, any relative displacements that lead to inaccuracies are excluded. The detachment of clamping devices and force indicator shortens the distance between the operator and patient and consequently facilitates handling during the surgical intervention. In the performing of NMR imaging, care should be taken that the clamping device and force indicator do not lead to artifacts and are reproduced in the image. The use of expensive materials are the inevitable consequence, which has led to the use of ceramic materials in the prior art. The same requirements then apply when imaging techniques are applied with the use of electromagnetic radiation. Here, too, the aim is to produce corresponding images that avoid artifacts. Due to the removal of the clamping device and force indicator before the imaging, the possibility is opened up of using conventional, and therefore inexpensive materials, which, as regards their functional possibilities, may be superior to the materials used in the prior art. Quality deficiencies therefore also arise in that, with a mechanical implementation of the force indicator, the inaccuracies in the indication of force are added to those of the clamping devices.

In a preferred embodiment of the clamping device, which is characterized by the simplicity of its construction and by reliable operating stability, a force action on the bolt by means of a helical spring, which is applied axially on the end face that is remote from the patent, and the opposite end of which bears against a counter-holder which is adjustable in an axial direction. The compression of the springs is generated by virtue of the displaceability of the counter-holder relative to the housing which forms the guidance for the bolt. If the counter-holder is moved towards the patient, a compression of the spring takes place, which leads to a force development, which acts on the end of the bolt and, by transmission thereof, presses the mandrel against the head of the patient with the same force. In the event of a change of the clearance of the counter-holder away from the patient, the spring relaxes and consequently leads to a reduction of the contact press force of the mandrel. Adjustment of the counter-holder permits a continuous adjustment of the contact-press force.

For the constructional implementation of the adjustable counter-holder, two possibilities are proposed:

On one hand, the counter-holder required for fixation of the patient's head is a screw pin, which meshes with a screw thread on the inner surface of the housing. The end face of the screw pin forms the counter-holder of the spring.

In an alternative, the counter-holder is formed by a hollow cylinder, the outer end face of which serves for forming the counter-holder. The hollow cylinder meshes with an internal/external thread of the housing and, by rotation, effects the axial adjustment of the counter-holder and consequently the influencing of the force exerted by the spring.

Another possibility consists in the fact that the hollow cylinder has an external thread, which passes through the fastening in the C-bend and meshes with a nut, which is screwed onto the hollow cylinder at the patient side and comes to lie in areal contact on the C-bend. The actuation of the nut effects an axial displacement of the hollow cylinder and consequently also of the counter-holder located therein. Due to the prevailing pressure torque, the nut is to be applied onto the hollow cylinder from the patient side.

In the above-described case of the derivation of the clamping forces from a compressed spring, the invention recommends, as a force indicator, the use of a pin, which, at its one end, cooperates directly or indirectly with the end, in each case, of the bolt and is guided outwardly via the counter-holder, the orientation of the pin taking place in the direction of movement of the bolt. On a compression of the spring, the distance between the bolt and counter-holder becomes smaller, with the result that the pin projects outwardly all the more. When the compression is relaxed, the distance between the bolt and counter-holder increases, with the result that the pin only projects by a shorter length. The length of the outwardly projecting end of the pin acts as an indicator for the force exerted on the patient by the spring and consequently also by the bolt with the mandrel disposed thereon.

The specific embodiment of the fixation means according to the invention is largely arbitrary within the scope of the invention, in so far as it fulfills the purpose of temporary arresting of the bolt. The bolt must, on one hand, be displaceable in an axial direction during the phase of clamping the head, however, subsequently, must be arrestable when the desired contact press force has been reached, as well as in the subsequent work phase (preparation of the image and/or performance of the surgical intervention). A preferred realization of the fixation means can be performed by means of a clamping block, which is moved towards the bolt essentially in a radial direction, and thereby effects a contact pressure, which, by virtue of the guidance of the bolt, results in a temporary clamping, and thereby arresting of the bolt. The manner in which the movement of the clamping block takes place is ultimately arbitrary within the scope of the invention. The generation of a clamping action, which leads to freedom from play, is crucial.

In an advantageous further embodiment, the cross-section of the bolt on the side opposite the clamping block, is formed as an edge and cooperates with a guide that is shaped so as to be complementary thereto. With the actuation of the clamping block, the edge is pressed into the complementary-shaped groove in the guide until it is in areal contact, and thereby effects a fixation of the bolt, in the case of both azimuthal and axial movement of the bolt. By virtue of the detachment of the connection by a radial movement of the clamping block away from the bolt, the latter is released and can be axially freely displaced again.

As an additional measure for fixation of the bolt, helical grooves and be introduced on the clamping block and, opposite them, screw threads formed complementary thereto, on the bolt, which are dimensioned such that they can be brought into mutual engagement. By means of this measure, in dependence on the orientation of the grooves, a further fixation of the bolt can be prevented on axial and/or azimuthal movements of the bolt. In the case of a circulating thread without a pitch, in which the grooves are thus only oriented in an azimuthal direction, axial movement of the bolt is prevented. Due to the geometry of the toothing, the interaction of the clamping block and bolt can only be effected in discrete steps. This disadvantage becomes acceptable if the toothing is sufficiently fine, that is to say where the teeth are correspondingly narrow.

It is advisable to choose the cross-section of the bolt in the manner of a polygon, in order, on one hand, to fulfill the requirement of developing an edge, and on the other hand to make a flat contact-pressure face available to the clamping block. Without restriction of the generality, triangular, pentagonal and heptagonal forms are suitable for this. The foremost goal for implementing the fixation means is the maximization of the fixation of the bolt on the C-bend.

The number of the mandrels defining contact points on the head of the patient is basically arbitrary within the scope of the invention. At least two mandrels located essentially diametrically opposite one another are necessary for fixation of the head. In general, one mandrel is rigid, that is to say spatially fixed, while the opposite mandrel is provided with the clamping device for generating the defined contact press force. Spring application to both mandrels is not very expedient, since, in the phase of fixation and generating the defined contact pressure, the increase of force on one side inevitably results in a yielding of the spring-loaded clamping device on the other side, which would result in a shifting of the position of the head, leading to inaccuracies in the positioning.

It is expressly possible for the individual mandrel to be replaced by a module that is provided with a plurality of mandrels and is designed as a rocker. The line of action of the rocker is described by the center perpendicular lines between the mandrels. The term "rocker" includes the possibility of attachment in a manner such that it is pivotable about a small angle.

In addition to the two mandrels that are disposed such that they are essentially diametrical to one another, further mandrels, which are essentially oriented differently therefrom are conceivable for additional fixation of the head.

As regard the materials, finally, it is proposed that the bolt, as well as its guide, is made of translucent materials, which are suitable for NMR application and/or for imaging with the aid of electromagnetic waves (e.g. x-ray, gamma). It is crucial that the clamping device and the force indicator remain free as regards the choice of material. The creation of artifacts and inaccuracies in the positioning are then reliably eliminated. As regards the handling, finally, it proves advantageous if the clamping device as well as the force indicator are accommodated in a common housing, because then it can be completely removed with the minimum outlay for detaching the fastening of the housing from the rest of the device.

Further details, features and advantages of the invention can be taken from the following descriptive part, in which an exemplary embodiment of the invention is explained with reference to the drawing, wherein.

Figure 1:
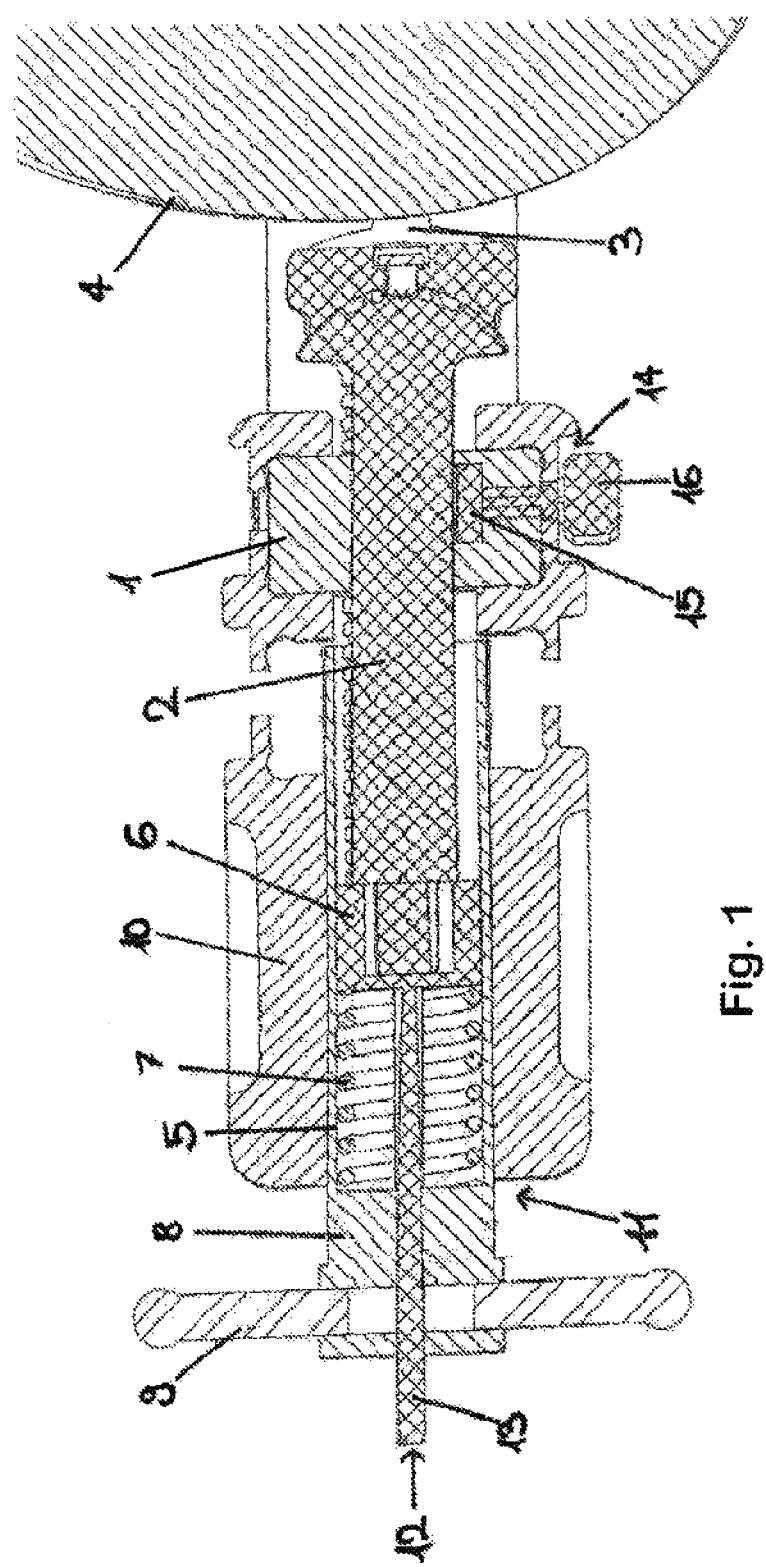
FIG. 1 shows axial longitudinal section through a device according to the invention.

FIG. 1 shows a schematic diagram of a head holder according to the invention with a clamped-in head of the patient in a side view resulting from a top view in the direction of the longitudinal body axis of the patient. The basic structure is formed in a manner known per se by the C-bend 1. Herein, essentially centrally, the head 4 of a patient is arrested and the C-bend 1 lies in an axial plane of intersection as regards the longitudinal axis of the body or of the head of the patient. In the left-hand end region of the C-bend 1, the arresting of the head according to the invention is shown, which, starting from the head 4 of the patient, consists of two mandrels 3, which are disposed on the head 4 with a defined force and in a manner symmetrical to a central axis. The defined contact press force is generated in that the mandrels 3 are fastened on an axially movable bolt 2, which can be seen only with its outer end in the top view shown, since the remaining length through further components is essentially covered by the housing 10. The fixation of the axially displaceable bolt 2 is performed via a screw 16 which, in the end region of the C-bend 1, runs perpendicular to the bolt 2. If the screw 16 is screwed in, the bolt 2 is fixed and a freedom from play results. The contiguous, essentially hollow-cylindrical housing 10 is provided with a slit that runs in a segmented manner, in which the screw 16 runs, the slit opening up the possibility that the housing 10 can be pulled off the device in a radial direction.

At that end of the housing 10 lying opposite the bolt 2, a counter-holder 8 can be seen, which is formed in the manner of a hollow cylinder 5 that is closed at its end, and of which, in the interior, the helical spring 7 is disposed, which is not drawn because of the side view. At the outer end of the cylinder or counter-holder 8, an actuating handle 9, which runs perpendicular to the plane of the drawing, is illustrated, with the aid of which a screwing movement of the counter-holder 8, or of the hollow cylinder 5 that forms the latter, relative to the C-bend 1 or bolt 2 is possible. Outwardly, a pin 13 projects in an axial direction, which, at it surface, is provided with a force indicator 12. The axial displaceability of the pin 13 serves as a force indicator 12 of the force that is exerted on the head 4 by means of the bolt 2 and the mandrels 3. The interaction of the individual elements can be clearly seen from the view shown below in FIG. 2. With the aid of the housing 10, it becomes possible to remove the clamping device 11 and force indicator 12, with the arrested bolt 2, the screw 16 and the fixation means 14 respectively as well as the arrested bolt 2 remaining firmly connected to the C-bend 1, with the result that the contact pressure on the head 4 of the patient is retained, despite the elimination of the clamping device 11.

Opposite that portion of the fixing arrangement which is described above and generates a defined contact pressure via an axially displaceable bolt 2 on the left-hand side there is disposed a further fixing arrangement, which forms a support and, starting from the head 4, consists of the mandrels 3, which are fastened on a counter-bolt 17, which is also axially moveable, the latter being slidable in an axial direction relative to the C-bend 1. The axial fixation here is performed by means of a union nut 18, which meshes with the thread of the counter-bolt 17, and, from the patient side, lies firmly against the C-bend 1. As a result, a rigid fixation of the right-hand mandrels 3 is obtained. A change of the contact press force is possible in principle by actuating the counter-nut 18, however no defined clamping force can be adjusted. The object of the counter-nut 18 is an adaptation to the specific anatomical conditions of the patient to be examined.

Figure 2:
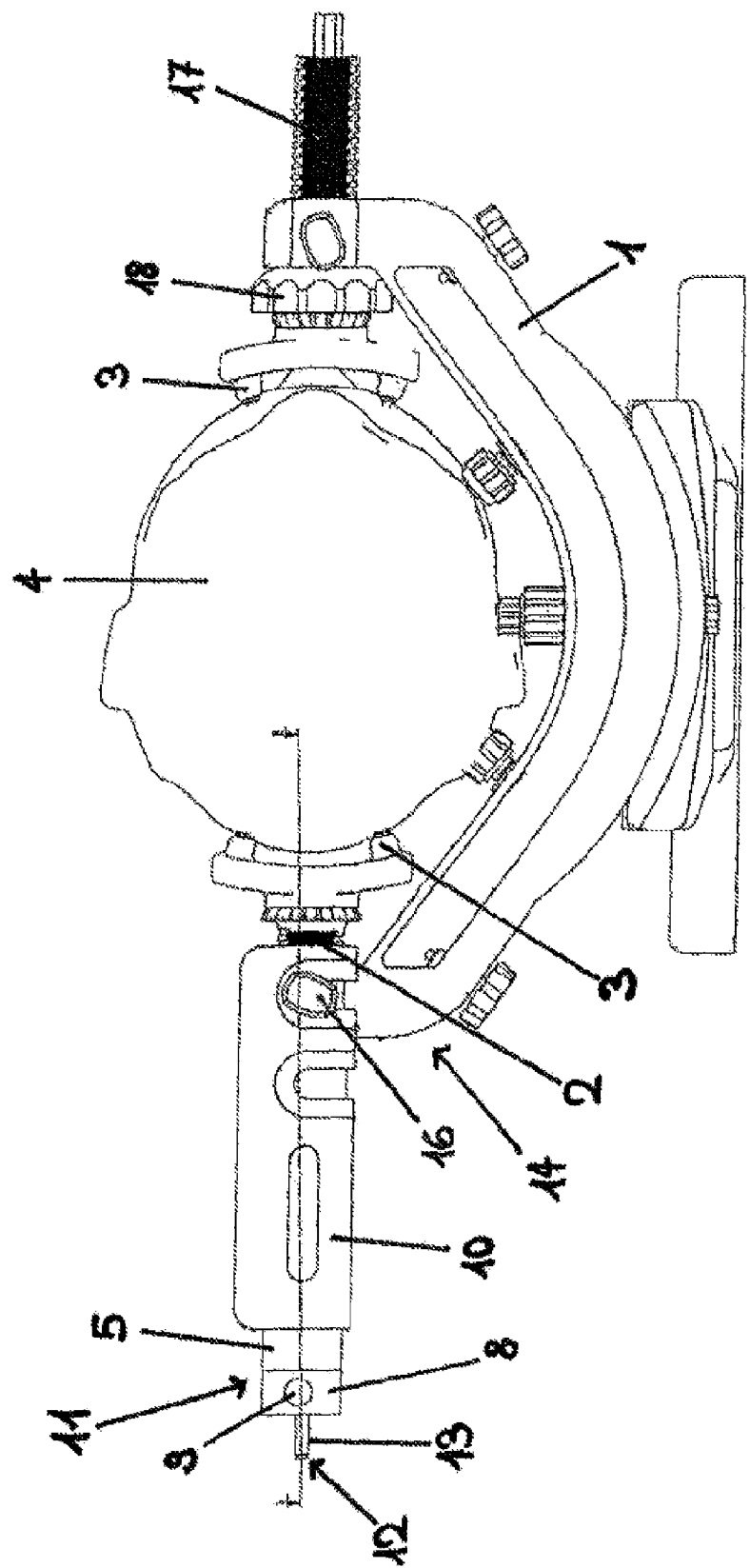
FIG. 2 shows a top view in the direction of the body axis of a patient.

The function of the device described in FIG. 1 can be seen much more clearly with reference to the diagram in FIG. 2. The device, which is only illustrated as a partial section, is shown in the phase of resting against the head of the patient. In accordance with the rules of technical drawing, the sectional faces are shown hatched. The approximately semi-circular C-bend 1 is oriented perpendicular to the plane of the drawing and encircles the head 4 of the patient. In the end region, the bolt 2 is shown, which extends in the plane of the drawing and, at its outer end, is provided with a mandrel 3, which, in turn, bears against the head 4 of the patient and thus shows the clamped-in state.

That end of the bolt 2 that lies opposite the patient engages in a piston 6, which is mounted such that it is displaceable in a hollow cylinder 5. On the end faces opposite the bolt 2, a helical spring 7 presses the piston 6 against the end face of the bolt 2. The piston 6 thus acts as a force mediator between the helical spring 7 and bolt 2, the contact in each case being produced by loose lying against.

The hollow cylinder 5 is sealed at its end which lies opposite the bolt 2, and in this manner forms the counter-holder 8 for the helical spring 7. As indicated via the actuating handle 9, the hollow cylinder 5 is guided via a screw thread within the housing 10, so that, with a screwing in of the hollow cylinder, the helical spring 7 undergoes compression and consequently the piston 6 presses with increased force against the bolt 2, which in turn presses the mandrel 3 against the head 4 of the patient. On a rotation of the actuating handle 9 in the opposite direction this leads to a relief of the helical spring 7 with the consequence that, according to the above-described mechanism, the contact press force of the mandrel 3 is reduced. The arrangement, consisting of the bolt 2 with, fastened thereon, the mandrel 3, piston 6 and helical spring 7, as well as, simultaneously, the hollow cylinder 5 forming the counter-holder 8, in their entirety describe the clamping device 11.

For exertion and monitoring of a defined contact press force of the mandrel 3 on the head 4 of the patient, a force indicator 12 is provided, which is performed mechanically and is formed by a pin 13 as indicator, which extends coaxially and in an extension to the bolt 2, is fastened on the piston 6, which passes through the helical spring 7 and projects outwardly via a suitable opening, which serves as guide. The length of the visible pin 13 can, as an indicator of the position of the piston 6, describe the force display exerted directly by the helical spring 7 and, by mediation of the piston 2, exerted on the mandrel 3. Corresponding index markings facilitate the assignment to numbers. The desired force adjustment can also be repeated in a reproducible manner.

When the desired contact pressure is reached, and thereby the end position of the mandrel 3, a fixation means 14, as a principal concept of the invention, is provided, which, in the illustrated exemplary embodiment, consists of a clamping block 15, which is moved via an eternally actuatable screw 16 in a radial direction towards the bolt 2, and presses against the latter. Herein, the clamping block 15 has to come into contact with the bolt 2 with such force that the bolt 2 remains spatially fixed in C-bend 1 under the influence of the forces acting on it. A reinforcement of the fixing is effected by toothings, which are integrally formed on the bolt 2, on the one hand, and, on the other hand, on that surface of the clamping block 15, which comes into contact.

According to a core idea of the present invention, the clamping device 11 with the force indicator 12, which are commonly carried in a housing 10, can, after detachment of the corresponding connections, which are not shown here, be readily removed from the C-bend 1 and the bolt 2 which is arrested therein. The distance, which is shown in the drawing, between the C-bend 1 and housing 10 illustrates the presence of two autonomous parts, wherein it is to be expressly completed that the bolt 2 is only in loose contact with the piston 6.

After the removal of the clamping device 11 and force display 12, the necessary work measures in the form of preparing images and/or making surgical interventions, can be performed.

As a result, a play-free and compact arrangement is produced, which provides considerable advantages over the prior art.

LIST OF REFERENCE CHARACTERS

1 C-bend
2 Bolt
3 Mandrel
4 Head
5 Hollow cylinder
6 Piston
7 Helical spring
8 Counter-holder
9 Actuating handle
10 Housing
11 Clamping device
12 Force indicator
13 Pin
14 Fixation means
15 Clamping block
16 Screw
17 Counter-bolt
18 Union nut

The invention claimed is:

1. A head holder for fixation of the head of patients for producing nuclear magnetic resonance (NMR) images, the head holder comprising a C-bend, at each end region of which at least one mandrel is fastened, wherein the at least one mandrel is substantially diametrically assigned with respect to each other and is coaxially fastened to a bolt received within a guide channel of a housing which guides axial movement of the bolt relative to the housing, and the housing is plugged onto an end portion of the C-bend, a clamping device configured to act upon the bolt in an axial direction, and a force indicator assigned to the clamping device, wherein fixation means are provided which serve to temporarily arrest the bolt, and wherein the clamping device including the housing and the force indicator are detachable from the head holder while retaining attachment of the bolt to the C-bend using the fixation means, and wherein the fixation means includes a clamping block, which is movable in a radial direction toward the bolt and contacts the bolt to produce a clamping effect, wherein a helical spring of the clamping device acts on the bolt and is supported via a counter-holder on an outer end face of a hollow cylinder, the hollow cylinder being axially adjustable relative to the housing and wherein the counter-holder is an end face of a screw pin, which meshes with an inner surface of the housing.

2. The head holder according to claim 1, wherein grooves are applied superficially on a contact surface of the bolt.

3. The head holder according to claim 2, wherein an orientation of the grooves is perpendicular to the direction of movement of the bolt.

4. The head holder according to claim 1, wherein a pin is in direct or indirect connection with the bolt and, via the counter-holder, is guided outwardly in the direction of movement of the bolt.

5. The head holder according to claim 1, wherein a cross-section of the bolt is chosen in a polygonal form.

6. The head holder according to claim 1, wherein the clamping device is only assigned to the mandrels of one side.

7. The head holder according to claim 1, wherein the at least one mandrel is replaced by a rocker equipped with a plurality of mandrels.

8. The head holder according to claim 1, wherein in addition to the mandrels that lie diametrically with respect to one another, further mandrels are attached.

9. The head holder according to claim 1, wherein the bolt, as well as a guide in the C-bend, consist of translucent material.

10. The head holder according to claim 1, wherein the clamping device and force indicator are accommodated in the housing.

11. The head holder of claim 1, wherein a cross-section of the bolt, on a side opposite the fixation means, is formed as an edge running in the axial direction and cooperates with the guide channel, which is shaped such that it is complementary thereto, of the housing.

12. A head holder for fixation of a head of a patient for producing nuclear magnetic resonance (NMR) images, the head holder comprising:
    a C-bend; and
    a clamping device comprising:
        a housing attached to the C-bend and including a guide channel;
        a counter-holder including a hollow cylinder supported in the guide channel and having an open end and a closed end;
        a bolt having a first end received within the hollow cylinder and a second end extending through the open end of the hollow cylinder having at least one mandrel, the bolt configured to move along an axis relative to the housing and the hollow cylinder;
        a spring within the hollow cylinder positioned between the first end of the bolt and the closed end of the hollow cylinder, wherein the hollow cylinder is movable along the axis relative to the housing to adjust an axial force that is applied to the bolt by the spring along the axis; and
        a force indicator, which indicates the axial force; and
        a clamping block which is moveable in a radial direction relative to the axis and contacts the bolt to fix a position of the bolt along the axis relative to the housing;
    wherein the housing including the counter-holder, the spring, and the force indicator is plugged onto an end portion of the C-bend and configured to be detached from the C-bend while attachment of the bolt to the C-bend is retained by the clamping block.

13. The head holder according to claim 12, wherein grooves are applied superficially on a contact surface of the bolt.

14. The head holder according to claim 13, wherein an orientation of the grooves is perpendicular to the direction of movement of the bolt.

15. The head holder according to claim 12, wherein a pin is in direct or indirect connection with the bolt and, via the counter-holder, is guided outwardly in the direction of movement of the bolt.

16. The head holder according to claim 12, wherein a cross-section of the bolt is chosen in a polygonal form.

17. The head holder according to claim 12, wherein the at least one mandrel is replaced by a rocker equipped with a plurality of mandrels.

18. The head holder according to claim 12, wherein the bolt, as well as a guide in the C-bend, consist of translucent material.

19. The head holder according to claim 12, wherein the clamping device and force indicator are accommodated in the housing.

20. A method for using the head holder according to claim 1, in which
    the head of the patient is positioned in the head holder;
    subsequently at least one mandrel is moved with a clamping device until a desired contact pressure is reached, wherein
        the bolt and consequently the at least one mandrel fastened therein are arrested by the fixation means;
    then the clamping device and the force indicator are removed from the head holder; and
    finally, actual work steps, taking of images and/or performing surgical interventions, are carried out.

* * * * *